United States Patent [19]

Chantler et al.

[11] 4,331,649

[45] May 25, 1982

[54] IMMUNE COMPLEX ASSAY

[75] Inventors: Shireen M. Chantler, London; William Edgar, West Wickham, both of England

[73] Assignee: Burroughs Wellcome Co., Research Triangle Park, N.C.

[21] Appl. No.: 82,489

[22] Filed: Oct. 9, 1979

[30] Foreign Application Priority Data

Oct. 10, 1978 [GB] United Kingdom ............... 39980/78

[51] Int. Cl.$^3$ ..................... G01N 33/50; G01N 33/54; G01N 33/68
[52] U.S. Cl. .................................... 424/12; 23/230 B; 424/8; 424/78; 424/85; 424/88
[58] Field of Search ..................... 424/7, 8, 12, 78, 85, 424/88; 23/230 B

[56] References Cited

U.S. PATENT DOCUMENTS

| | | | |
|---|---|---|---|
| 3,088,875 | 5/1963 | Fisk | 424/12 |
| 4,118,349 | 10/1978 | Bonacker | 424/12 X |
| 4,141,965 | 2/1979 | Soothill | 424/12 |
| 4,181,636 | 1/1980 | Fischer | 424/12 X |

FOREIGN PATENT DOCUMENTS

| | | |
|---|---|---|
| 1503547 | 3/1958 | United Kingdom . |
| 2004892 | 4/1979 | United Kingdom . |
| 2005275 | 4/1979 | United Kingdom . |
| 2027031 | 2/1980 | United Kingdom . |
| 2030293 | 4/1980 | United Kingdom . |

OTHER PUBLICATIONS

Chantler, J. Immunol. Methods, vol. 13, 1976, pp. 367–380.

*Primary Examiner*—Anna P. Fagelson
*Attorney, Agent, or Firm*—Donald Brown

[57] ABSTRACT

Method for the estimation of immune complex and analysis of a constituent thereof. Method comprises a latex particle agglutination test in which a reagent comprising low affinity latex particles is contacted with a sample containing immune complex. The low affinity coated latex particles are latex particles coated with IgG antibodies to the complex constituent and may be prepared by contacting latex particles with the IgG antibodies, the latter optionally being substituted with a coupling agent. One or more reagents are conveniently provided in kit form.

4 Claims, No Drawings

IMMUNE COMPLEX ASSAY

The present invention relates to the estimation of immune complexes and analysis of constituents thereof.

Immune antigen-antibody complexes have been implicated in the pathogenesis of many human diseases, and thus their detection and estimation is of central importance to the treatment of these diseases.

Levinsky and Soothill, *Clinical and Experimental Immunology*, 29, 428 (1977), Levinsky et. al., *New England J. Medicine*, 298, 126 (1978) describe a method for the estimation of an immune complex and analysis of a constituent thereof, in which sample containing immune complex is incubated with coated latex particles and IgM antibodies, the latex particles coated with said complex constituent and the IgM antibodies being low affinity non-human IgM antibodies to said complex constituent. The method constitutes a latex particle agglutination test in which presence of appropriate immune complexes in the sample is determined by their inhibition of agglutination of the coated latex particles, and this inhibition of agglutination may be monitored by use of a suitable electronic particle counting apparatus such as a Coulter counter.

An essential feature of the aforementioned test procedure is that it utilizes low affinity IgM antibodies and thereby is enabled to measure the antigen-antibody complexes without interference from the non-complexed components which may be present.

Whilst the use of IgM antibodies permits the differentiation described above they suffer from the disadvantage that they are produced in relatively small quantities in animals and must be collected soon after injection. Thus injection of a large number of animals followed by careful timing of collection is essential if adequate quantities of IgM antibodies are to be obtained. A further disadvantage of IgM antibodies is that when coated onto latex the resultant particles are unstable and have a limited shelf life.

In contrast IgG antibodies may be produced in much larger quantities in animals and as they are the end product of immunisation the period of collection is much less critical. In addition when coated onto latex the resultant particles are generally recognised as comparatively stable and thus have a longer shelf life. However, IgG antibodies are high affinity antibodies and thus in the past have been generally considered as unsuitable for use in the test methods described above as they would not be capable of differentiating between complexes and their non-complexed components.

We have now surprisingly found, contrary to the teaching of the prior art, that high affinity IgG antibodies may be used in the estimation of immune complexes in a direct agglutination technique, a development of the aforementioned method. The present invention therefore provides, in a first aspect, a method for the estimation of an immune complex and analysis of a constituent thereof comprising a latex particle agglutination test in which a reagent comprising low affinity coated latex particles is contacted with a sample containing immune complex, the low affinity coated latex particles comprising latex particles coated with IgG antibodies to the complex component in an amount sufficient to render the resultant particles of low affinity.

The term "low affinity" as used in referring to the coated latex particles used in the present invention means having insufficient binding energy in reaction with non-complexed antigens to cause visible agglutination of the particles. Thus the particles are comparable to particles obtained by coating latex with low affinity IgM antibodies.

Any constituent of the immune complex may be analysed by the present method, provided the constituent can be used to produce IgG antibodies and provided these antibodies are capable of attachment to latex particles. Thus the immuno-globulin constituent e.g. IgG, IgM or IgA, or complement components e.g. $C_3$, of complex may be analysed by the present method. The method may also be employed for analysis of antigen constituents of complex, for instance for analysis of viral, bacterial or other antigenic materials giving rise to immune complex formation.

Immune complexes are believed to cause disease symptoms, especially tissue damage, and thus the method may be employed for diagnosis of immune complex associated diseases. In a preferred embodiment the method may provide a simple and easily applied test e.g. a slide agglutination test, for such diagnosis and for screening large populations for incidence of immune complex associated diseases or presence of antigen antibody complex. The method may also be used to monitor the effect of treatment e.g. chemotherapy, plasmapheresis or immunological removal of complex, upon the levels of immune complex e.g. present in a patient's bloodstream.

The coated latex particles used in the method of the present invention are prepared by linking the IgG antibodies to latex or similar particles, and are characteristically in a form suitable for latex particle agglutination tests. Some of these antibodies may undergo spontaneous attachment on contact with latex particles at various temperatures, through it may be desirable to employ a coupling reagent to link the antibodies to latex particles. Any suitable coupling reagent may be employed, dependent upon the nature of the reactive group on the latex particle.

Although any suitable latex particles may be used in the present invention it is preferred that the particles have a size of less than $2\mu$. In particular particles of less than $1\mu$ are suitable for the purpose of the present invention. Particularly suitable latex particles are Estapor K 150 latex (Rhone-Poulenc-Polymeres), ($0.8\mu$).

The amount of IgG antibody which will be required to be coupled to the latex particles to produce a low affinity coated latex particle for use in the present invention will of course vary not only with the particular IgG antibody used but also with the particular latex particles employed. The optimum concentrations of such IgG antibodies in each particular case may be readily determined by methods well known in the art. As a general rule however such concentrations will be expected to be below 200 $\mu$g of IgG per mg of latex and may for instance frequently be below 50 $\mu$g per mg, for example 2 to 10 $\mu$g per mg of latex.

The IgG antibodies which are coupled to latex particles for use in the immune complex assay method are raised in suitable animals to the constituent of complex which is undergoing analysis. For laboratory purposes small animals such as guinea pigs or, especially, rabbits have been found to be satisfactory for production of these antibodies. However larger animals such as cows, horses and particularly sheep may be more desirable for large scale production. Although in certain cases it may be desirable to use IgG antibodies derived from humans, in general it is preferred that the antibodies be of non-human origin. Generally the immune complex constituent, preferably in purified form, is injected into the animal, the animal subsequently bled and IgG separated out of the antiserum. Advantageously the yield of IgG may be optimised having regard to various factors as will be apparent to skilled workers in the art. For instance, the concentration of immune complex constituent injected into the animal, the use of adjuvants, and the site and number of and intervals between injections may affect the subsequent yield of antibody. For the preferred method using multiple injections in rabbits or sheep periods of from about two months after the first injection onwards having been found to be appropriate for satisfactory IgG production after injection of human immuno globulin, classes IgA and IgG, in Freund's complete adjuvant. Satisfactory serum may also be obtained by a single injection schedule and in such cases a period of about two weeks after injection has been found to be satisfactory. Generally it is also believed that similar periods are appropriate for satisfactory IgG production with other immune complex constituents.

Characteristically the IgG antibodies interact specifically with the complex constituent to which they have been raised, and this interaction is typically readily reversible unless the constituent is in an aggregated form e.g. as a component of an immune complex. Thus, on mixing, the IgG antibody coated latex particles conveniently interact strongly with any immune complex present in the mixture comprising the particular constituent. Thus immune complexes may be estimated and their constituents analysed by the agglutination of latex particles which they cause, the greater the concentration and availability of immune complex constituents the greater the agglutination of the latex particles. For example, samples containing immune complex are contacted with the coated latex particles and agitated after which agglutination is monitored by any suitable technique.

Generally it is desired to determine immune complexes as a component of a patient's bloodstream, through the present invention may be equally well applied to the determination of immune complexes in other media including other physiological fluids such as urine. Thus samples derived from serum or other physiological fluid may require suitable preparation before use in the immune complex test.

After preparatory treatment, if required, samples e.g. serum samples, are contacted with the coated latex particles and agitated. The agitated mixture is generally aqueous and agitation is carried out for a period sufficient to complete reaction.

Subsequent to agitation the agglutination of latex particles may be monitored by any suitable means. For example, in preferred embodiment, a simple slide agglutination procedure may be employed, conveniently relying upon a straightforward visual comparison. Alternatively, other quantitative methods known in the art may also be used.

The coated latex particle products used in the method of the invention are novel per se and are included within the scope of the invention. These products characteristically comprise latex particles coated with IgG antibodies to complex constituents in an amount sufficient to render the resultant coated particles of "low affinity" as defined herein. The products are typically in a form suitable for latex particle agglutination test.

The reagents for use in the immune complex assay of the present invention may be supplied to the user in the form of kits and such kits are included within the scope of the invention. Such kits typically comprise low affinity latex particles coated with IgG antibodies to the constituent of complex undergoing analysis, and may also conveniently comprise appropriate buffer solutions for use in the method and possibly also control samples of known activity and suitable slides for use in the slide agglutination adaptation of the method. Generally, also, kits may be supplied for estimation of a range of different types of immune complex and analysis of a range of complex constituent and thus may comprise a corresponding range of different latex particle reagents coated with the corresponding range IgG antibodies to the desired complex constituents. Usually these kits are supplied together with instructions or other indications to enable the user to carry out the assay method which advantageously requires little laboratory experience.

The invention is illustrated by the following Examples which should not be interpreted as limiting the invention in any way.

EXAMPLE I

Preparation of Latex-antibody reagent for measurement of immune complexes containing IgG A. Preparation of anti-human IgG serum in sheep and rabbits Antisera were prepared in sheep and rabbits using two different immunisation schedules outlined below. In the first schedule a single injection of antigen was used; in the other multiple injections of antigen were given over a period of two to three months.

| Species used | Immunisation Schedules | |
|---|---|---|
| | Day | Treatment |
| Schedule 1 | | |
| Sheep | 0 | Injection 1: 40 mg human IgG in 4 ml Freunds Complete Adjuvant (FCA), given by intramuscular route in 4 sites. |
| | 10–11 | Test Bleed: 10 ml blood taken, serum removed and checked for activity. |
| Sheep | 12 | Bleed: 500 mls taken for use. |
| Rabbit | 0 | Injection 1: 10 mg human IgG in 1 ml FCA given by intramuscular route at 2 sites. |
| | 10 & 12 | Test bleeds: 5 ml blood taken to test for activity. |
| | 11–15 | Bleed out suitable animals. |
| Schedule 2 | | |
| Sheep | 0 | Injection 1: 2 mg H-chain of human IgG + 3 ml FCA given by intramuscular route at 2–4 sites. |
| | 28 | Injection 2: 1 mg H-chain + 3 ml FCA as above. |
| | 56–70 | Injection 3: As for injection 2. |
| Sheep | 70–84 | Test bleeds were taken approximately 2 weeks after injection 3 and tested for activity. Large bleeds were taken from selected animals for use. |
| Rabbit | 0 | Injection 1: 2 mg human IgG in FCA by intramuscular route at 2 sites. |
| | 28 | Injection 2: 1–2 mg human IgG as above. |
| | 56 | Injection 3: As above |
| | 70–74 | Test bleeds taken to check activity. Large samples taken from selected animals. |

Immunising Antigen: Either H-chain preparations derived from human IgG and obtained from Worthington Corp Ltd. or human IgG prepared by ion exchange Chromatography from a pool of normal human serum was used.

Processing of bleeds: Blood samples taken from immunised animals were allowed to clot after which the serum was removed. In some cases the serum was made immunospecific for the IgG class of immunoglobulin ($\gamma$-chain) by affinity chromatography using an insoluble absorbent comprised of normal human serum depleted of IgG, chemically coupled to Sepharose 4B.

Preliminary testing of serum activity

This is done by a direct slide agglutination test using one drop of latex-human IgG and serial dilutions of the antiserum. Agglutination is read after 2 minutes gentle rocking of the slide and recorded as follows:

|  | Dilution of Antiserum | | | | | |
| --- | --- | --- | --- | --- | --- | --- |
|  | 1/50 | 1/100 | 1/200 | 1/400 | 1/800 | 1/1600 |
| Serum 1 | +++ | ++ | ++ | + | − | − |
| Serum 2 | +++ | +++ | +++ | ++ | + | − |
| Normal Serum | − | − | − | − | − | − |

B. Preparation of IgG fraction from sheep and rabbit antisera

The IgG fraction from the antiserum was obtained by salt precipitation followed by DEAE cellulose chromatography. Saturated ammonium sulphate was added slowly to antiserum to a final concentration of 45% saturation. The precipitate containing the IgG fraction was removed by centrifugation and dissolved in 0.015 M $KH_2PO_4$ pH 8.0 followed by dialysis overnight against 50 volumes of this buffer. The solution was applied to a column of DEAE cellulose equilibrated with 0.015 M $KH_2PO_4$ pH 8.0 and eluted with a buffer gradient of 0.015 M to 0.3 M $KH_2PO_4$ pH 8.0. The first peak contained only IgG as determined by immunoelectrophoresis and was collected.

C. Preparation of latex-antibody suspensions

1. Estapor K150 latex particle size 0.8$\mu$ (Rhone-Poulenc-Polymeres) was obtained at a concentration of 10% latex and diluted to 2% latex with 0.27 M glycine-saline pH 8.2.

2. The correct concentration of IgG to be added to the latex was determined by performing a trial sensitisation. Increasing quantities of the IgG fraction, from 2 $\mu$g/mg of latex to 20 $\mu$g/mg of latex are added to a suspension of 2% latex in glycine-saline buffer. The results are shown in Table 1.

TABLE 1

| | Range of concentrations of sheep or rabbit IgG used for sensitisation of latex | | | |
| --- | --- | --- | --- | --- |
| Tube No. | K150 10% | IgG Anti IgG | | Buffer |
| 1 | 0.2 | 0.040 | (2$\mu$g/mg) | 0.76 |
| 2 | 0.2 | 0.080 | (4$\mu$g/mg) | 0.72 |
| 3 | 0.2 | 0.120 | (6$\mu$g/mg) | 0.68 |
| 4 | 0.2 | 0.200 | (10$\mu$g/mg) | 0.60 |
| 5 | 0.2 | 0.300 | (15$\mu$g/mg) | 0.50 |
| 6 | 0.2 | 0.400 | (20$\mu$g/mg) | 0.40 |

3. The latex: antibody suspensions were incubated at 60° C. for 30 minutes and cooled to room temperature.

4. An equal volume of glycine-saline buffer containing 0.1% bovine serum albumin was added and the suspension was sonicated for 20 seconds to remove granularity of the latex and provide a smooth suspension.

5. The sensitivity of the latex reagents was checked with aggregated IgG, monomer IgG and normal human serum undiluted and at 1:5 and 1:10 dilutions.

(i) Aggregated IgG was prepared by treating Kabi IgG with sodium hydroxide at pH 12.9 for 30 minutes. The high molecular weight aggregated IgG was separated by chromatography on Sepharose Cl6B.

(ii) Doubling dilutions of aggregated IgG were prepared in glycine saline buffer giving concentrations from 28 $\mu$g/ml to 3 $\mu$g/Ml. Monomer IgG was diluted to concentrations of 3 mg/ml, 1 mg/ml and 0.1 mg/ml. Normal human serum was diluted 1 in 5 and 1 in 10 glycine-saline.

(iii) The test was carried out by placing one drop of each dilution of aggregated IgG, momomer IgG or serum on a glass slide and adding 1 drop of latex reagent. This was mixed and rocked gently for 2 minutes while observing from macroscopic agglutination of the latex.

The correct concentration of serum IgG for sensitisation is obtained by selecting the latex suspension which shows agglutination with all levels of aggregated IgG preferably down to 3 $\mu$g/ml whilst showing no agglutination of the non-complexed constituent. The results are shown in Table 2.

TABLE 2

| | Sensitivity of different latex-antibody preparations with monomer and aggregated IgG and with normal serum | | | | | | | |
| --- | --- | --- | --- | --- | --- | --- | --- | --- |
| $\mu$g IgG per mg latex | Aggregated IgG $\mu$g/ml | | | | Monomer IgG mg/ml | | serum | |
| | 28 | 14 | 7 | 3 | 3 | 1 | undilute | 1:10 |
| 2 | ++ | ++ | + | + | +(−) | +(−) | +(−) | +(−) |
| 4 | +++ | +++ | ++ | + | +− | +− | +− | +− |
| 6 | +++ | +++ | ++ | + | +− | +− | +− | +− |
| 10 | +++ | +++ | ++ | + | +− | +− | +− | +− |
| 15 | +++ | +++ | ++ | +− | − | − | − | − |
| 20 | ++ | + | +− | − | − | − | − | − |

In this example sensitisation at 15 $\mu$g/ml differentiaties between aggregated and monomer IgG.

Example of agglutination patterns with latex sensitised with antibody derived from different antisera.

$\mu$g IgG (a) Latex-rabbit IgG anti IgG (Schedule 1)

-continued

| per mg latex sensitised | Aggregated IgG μg/ml | | | | Monomer IgG | | serum | |
|---|---|---|---|---|---|---|---|---|
| | 28 | 14 | 7 | 3 | 3 | 1 | undilute | 1:10 |
| 2 | ++ | ++ | + | + | + | + | + | + |
| 4 | +++ | ++ | + | +− | − | − | − | − |
| 6 | +++ | ++(+) | + | +− | − | − | − | − |
| 10 | +++ | +(+) | + | + | + | + | +(−) | +(−) |
| 15 | ++ | ++ | + | + | + | + | + | + |
| 20 | ++ | ++ | ++ | ++ | +(+) | +(+) | +(+) | +(+) |

(b) Latex-rabbit IgG anti IgG (Schedule 2)

| μg IgG per mg latex sensitised | Aggregated IgG μg/ml | | | | Monomer IgG | | serum | |
|---|---|---|---|---|---|---|---|---|
| | 28 | 14 | 7 | 3 | 3 | 1 | undilute | 1:10 |
| 2 | ++ | ++ | + | + | +(−) | +(−) | +(−) | +(−) |
| 4 | +++ | +++ | ++ | + | +− | +− | +− | +− |
| 6 | +++ | +++ | ++ | + | +− | +− | +− | +− |
| 10 | +++ | +++ | ++ | + | +− | +− | +− | +− |
| 15 | +++ | +++ | ++ | +− | − | − | − | − |
| 20 | ++ | + | +− | − | − | − | − | − |

(c) Latex-sheep IgG anti IgG (Schedule 1)

| μg IgG per mg latex sensitised | Aggregated IgG μg/ml | | | | Monomer IgG | | serum | |
|---|---|---|---|---|---|---|---|---|
| | 28 | 14 | 7 | 3 | 3 | 1 | undilute | 1:10 |
| 2 | +++ | + | + | + | + | + | + | + |
| 4 | +++ | +++ | ++ | + | − | − | − | − |
| 6 | +++ | +++ | ++ | + | − | − | − | − |
| 10 | ++ | ++ | + | +− | − | − | − | − |
| 20 | ++ | ++ | + | + | +(−) | | +(−) | +(−) |

(d) Latex-sheep IgG anti IgG (Schedule 2)

| μg IgG per mg latex sensitised | Aggregated IgG μg/ml | | | | Monomer IgG | | serum | |
|---|---|---|---|---|---|---|---|---|
| | 28 | 14 | 7 | 3 | 3 | 1 | undilute | 1:10 |
| 2 | +++ | + | + | + | + | + | + | + |
| 4 | +++ | +++ | ++ | +(+) | − | − | − | − |
| 6 | +++ | +++ | ++ | +(+) | − | − | − | − |
| 10 | +++ | +++ | ++ | + | − | − | − | − |
| 20 | ++ | ++ | + | + | + | + | +− | + |

EXAMPLE 2

Measurement of Immune Complex in Human Sera

Serum samples were obtained from normal patients and from patients considered to have immune complexes. Each serum sample was tested by placing one drop of serum on a glass slide and adding 1 drop of latex reagent prepared as described in Example I from K 150 latex and either sheep or rabbit IgG anti IgG obtained as described in Example I. The drops were mixed and the slide rocked gently for two minutes whilst observing for macroscopic agglutination of the lates. The agglutination was visually scored on a scale of − (no agglutination) to +++. The results are given below.

| Patient No. | Assessment | Latex reagent (IgG anti IgG-latex) | |
|---|---|---|---|
| | | Rabbit | Sheep |
| 1 | Normal | − | − |
| 2 | Normal | − | − |
| 3 | Normal | − | − |
| 4 | Normal | − | − |
| 5 | Disease | + | + |
| 6 | Disease | +++ | ++ |
| 7 | Disease | + | + |
| 8 | Disease | ++ | ++ |

We claim:

1. A method for the estimation of an immune complex and analysis of a constituent thereof comprising a latex particle agglutination test in which a reagent comprising low affinity latex particles is contacted with a sample containing immune complex, the low affinity latex particles comprising latex particles coated with IgG antibodies to the complex constituent in an amount of from 2 to 10 μg per mg of latex.

2. A method according to claim 1 in which the IgG antibodies are of non-human origin.

3. A method according to either claim 1 or claim 2 wherein the complex constituent is selected from the group consisting of an immunoglobulin constituent, a complement constituent or an antigen constituent.

4. A method according to claim 1 wherein the agglutination test comprises a slide agglutination test.

* * * * *